US008771735B2

(12) United States Patent
Rourke et al.

(10) Patent No.: US 8,771,735 B2
(45) Date of Patent: *Jul. 8, 2014

(54) IMMEDIATE RELEASE DOSAGE FORMS OF SODIUM OXYBATE

(75) Inventors: Andrea Rourke, San Mateo, CA (US); Clark Allphin, Los Altos, CA (US); Maura Murphy, Baltimore, MD (US)

(73) Assignee: Jazz Pharmaceuticals, Inc., Palo Alto, CA (US)

( * ) Notice: Subject to any disclaimer, the term of this patent is extended or adjusted under 35 U.S.C. 154(b) by 501 days.

This patent is subject to a terminal disclaimer.

(21) Appl. No.: 12/264,709

(22) Filed: Nov. 4, 2008

(65) Prior Publication Data

US 2010/0112056 A1 May 6, 2010

(51) Int. Cl.
*A61K 9/36* (2006.01)

(52) U.S. Cl.
USPC .......................................................... 424/479

(58) Field of Classification Search
USPC .......................................................... 424/479
See application file for complete search history.

(56) References Cited

U.S. PATENT DOCUMENTS

| | | | |
|---|---|---|---|
| 3,051,619 A | 8/1962 | Laborit | |
| 4,374,441 A | 2/1983 | Carter et al. | |
| 4,393,236 A | 7/1983 | Klosa | |
| 4,738,985 A | 4/1988 | Kluger et al. | |
| 4,916,161 A * | 4/1990 | Patell | 514/570 |
| 4,983,632 A | 1/1991 | Gessa et al. | |
| 5,294,430 A | 3/1994 | Borch et al. | |
| 5,380,937 A | 1/1995 | Koehler et al. | |
| 5,594,030 A | 1/1997 | Conte et al. | |
| 5,753,708 A | 5/1998 | Koehler et al. | |
| 5,840,331 A | 11/1998 | Van Cauter et al. | |
| 5,990,162 A | 11/1999 | Scharf | |
| 6,384,020 B1 * | 5/2002 | Flanner et al. | 514/53 |
| 6,436,998 B1 | 8/2002 | Cacciaglia et al. | |
| 6,472,431 B2 | 10/2002 | Cook et al. | |
| 6,472,432 B1 | 10/2002 | Perricone | |
| 6,780,889 B2 | 8/2004 | Cook et al. | |
| 7,262,219 B2 | 8/2007 | Cook et al. | |
| 7,568,822 B2 | 8/2009 | Ibrahim | |
| 7,851,506 B2 | 12/2010 | Cook et al. | |
| 8,263,650 B2 | 9/2012 | Cook et al. | |
| 8,324,275 B2 | 12/2012 | Cook et al. | |
| 8,461,203 B2 | 6/2013 | Cook et al. | |
| 2004/0092455 A1 | 5/2004 | Mamelak et al. | |
| 2005/0031688 A1 | 2/2005 | Ayala | |
| 2005/0142192 A1* | 6/2005 | Benjamin et al. | 424/464 |
| 2006/0018933 A1 | 1/2006 | Vaya et al. | |
| 2006/0024365 A1 | 2/2006 | Vaya et al. | |
| 2006/0210630 A1* | 9/2006 | Liang et al. | 424/468 |
| 2007/0270491 A1 | 11/2007 | Cook et al. | |
| 2008/0069871 A1 | 3/2008 | Vaughn et al. | |
| 2008/0292700 A1 | 11/2008 | Nghiem et al. | |
| 2008/0293698 A1 | 11/2008 | Johnson | |
| 2011/0039929 A1 | 2/2011 | Cook et al. | |
| 2011/0111027 A1 | 5/2011 | Rourke et al. | |
| 2012/0020833 A1 | 1/2012 | Cook et al. | |
| 2012/0076865 A1 | 3/2012 | Allphin et al. | |
| 2012/0202879 A1 | 8/2012 | Cook et al. | |
| 2012/0202880 A1 | 8/2012 | Cook et al. | |

FOREIGN PATENT DOCUMENTS

| | | |
|---|---|---|
| EP | 0235408 | 9/1987 |
| EP | 0344704 | 12/1989 |
| EP | 0616804 | 9/1994 |
| EP | 0635265 | 1/1995 |
| EP | 1140061 | 10/2001 |
| GB | 922029 | 3/1963 |
| JP | 57042651 | 3/1982 |
| JP | 04049212 | 2/1992 |
| JP | 05508422 | 11/1993 |
| RU | 2210360 | 8/2003 |
| WO | WO 96/40105 | 12/1996 |
| WO | WO 2006/053186 | 5/2006 |
| WO | WO 2010/053691 | 5/2010 |
| WO | WO2011/119839 | 9/2011 |
| WO | WO2011/139271 | 11/2011 |

OTHER PUBLICATIONS

Notification of Transmittal of the International Search Report and the Written Opinion of the International Searching Authority issued Dec. 18, 2009 in International Application No. PCT/US2009/061312.
Notification of Transmittal of the International Search Report and the Written Opinion of the International Searching Authority issued Jan. 18, 2011 in International Application No. PCT/US2010/033572.
Broughton, et al. "Gamma-Hydroxy-Butyrate in the Treatment of Narcolepsy: a Preliminary Report," (1976) Narcolepsy, NY, N.Y., Spectrum Publications, Inc. (1976) 659-668.
Broughton, et al. "The Treatment of Narcolepsy-Cataplexy with Nocturnal Gamma-Hydroxybutyrate," (1979) Can J. Neurol Sci (1979) 6:1-6.
Broughton, et al. "Effects of Nocturnal Gamma-Hydroxybutyrate on Sleep/Waking Patterns in Narcolepsy-Cataplexy," (1980) Can J. Neurol Sci (1980) 7:23-30.
Frucht, et al. "A Pilot Tolerability and Efficacy Trial of Sodium Oxybate in Ethanol-Responsive Movement Disorders," (2005) Movement Disorders, 20(10):1330.
L. Borgen, et al. "Xyrem® (sodium oxybate): A Study of Dose Proportionality in Healthy Human Subjects," (2000) J, Clin. Pharmacol., 40:1053.
Mamelak, et al. "The Effects of y-Hydroxybutyrate on Sleep," (1977) Biol Psych (1977) 12:273-288.

(Continued)

*Primary Examiner* — David J Blanchard
*Assistant Examiner* — Devang Thakor
(74) *Attorney, Agent, or Firm* — Seed IP Law Group PLLC

(57) ABSTRACT

The present invention provides a pharmaceutical composition, presented as a solid unit dosage form adapted for oral administration of sodium oxybate. The preferred unit dosage form is a tablet comprising a relatively high weight-percentage of sodium oxybate, in combination with a relatively small weight-percentage of total excipients. This permits the tablets to contain/deliver a pharmaceutically effective amount, e.g., about 0.5-1.5 g of sodium oxybate in each tablet with a delivery profile similar to that of the liquid form. The tablets are bioequivalent to the liquid form.

19 Claims, 2 Drawing Sheets

(56) References Cited

OTHER PUBLICATIONS

Remington. The Science and Practice of Pharmacy. 20th Edition, Gennaro, Ed,. Lippincott Williams & Wilkins (2000). (See e.g. p. 861).

Scharf, et al., "Effect of Gamma-Hydroxybutyrate on Pain, Fatigue, and the Alpha Sleep Anomaly in Patients with Fibromyalgia," (1998) J. Rheumatol. (1998) 25:1986-1990.

Notification Concerning Transmittal of International Preliminary Report on Patentability issued Nov. 15, 2012 in International Application No. PCT/US2010/033572.

First Office Action issued Feb. 27, 2013 in U.S. Appl. No. 13/071,369.

Response to First Office Action issued Feb. 27, 2013 in U.S. Appl. No. 13/071,369, filed May 28, 2013.

Notification Concerning Transmittal of the International Preliminary Report on Patentability issued Oct. 4, 2012 in International Application No. PCT/US2011/029802.

First Office Action issued Oct. 5, 2012 in Continuation U.S. Appl. No. 12/773,599.

Response to First Office Action filed Jan. 4, 2013 in Continuation U.S. Appl. No. 12/773,599.

Final Rejection issued May 13, 2013 in Continuation U.S. Appl. No. 12/773,599.

Arena, et al., "Absorption of Sodium Y-Hydroxybutyrate and its Prodrug Y-Butyrolactone: Relationship Between In Vitro Transport and In Vivo Absorption," Journal on Pharmaceutical Sciences, 69(3), Mar. 1980, 356-358.

Bedard, "Nocturnal y-Hydroxybutyrate—Effect on Periodic Leg Movements and Sleep Organization of Narcoleptic Patients," Clin Neuropharmacol., 12(1), Feb. 1989, 29-36.

Berner, Jon E., "A Case of Sodium Oxybate Treatment of Tardive Dyskinesia and Bipolar Disorder," J. Clin, Psychiatry, 2008, 69:5, p. 862.

Berthier, et al., "Possible Involvement of a Gamma-Hydroxybutyric Acid Receptor in Startle Disease," Acta Paediatr, 83, 1994, 678-680.

Ferrara, S. D., et al., "Pharmacokinetics of Y-Hydroxybutyric Acid in Alcohol Dependent Patients After Single and Repeated Oral Doses," Br. J. Clin, Pharmacol., 34, (1992), 231-235.

Ferris, T.J., et al., "Synthesis, characterisation and detection of gamma-hydroxybutyrate salts," Forensic Science International, 2012, 216: 158-162.

Frucht, S.J., et al., "A Single-Blind, Open-Label Trial of Sodium Oxybate for Myoclonus and Essential Tremor," Neurology, 2005, 65: 1967-1970.

Gallimberti, L., "Gamma-Hydroxybutric Acid in the Treatment of Alcohol Dependence: A Double-Blind Study," Alcohol Clint. Exp. Res., 16(4), (1992), 673-676.

Gallimberti, L., "Gamma-hydroxybutyric Acid for Treatment of Alcohol Withdrawal Syndrome," Clinical Pharmacology, 2(8666), (1989), 787-789.

Gerra, G., et al.,"Flumazenil effects on growth hormone response to gamma-hydroxybutyric acid," Int Clin Psychopharmacol., 9(3), (Sep. 1994), 211-5.

Gessa, G. L., et al., "Gamma-hydroxybutyric acid(GHB) for treatment of ethanol dependence," European Neuropsychopharmacology, 3(3), (1993), 224-225.

Gessa, G. L., "Gamma-hydroxybutyric Acid in the Treatment of Alcohol Dependence," Clin. Neuropharm., 15 Suppl 1 Pt A, 1992), 303a-304a.

Grove-White, I. G., "Critical Flicker Frequency after Small Doses of Methohexitone, Diazepam and Sodium 4-Hydroxybutyrate," Brit. J. Anaesth, 43(2), (1971), 110-2.

Grove-White, I. G., et al., "Effect of Methohexitone, Diazepam and Sodium 4-Hydroxybutyrate on Short-Term Memory," Brit, J. Anaesth, 43(2), (1971), 113-116.

Hasenbos, M. A., et al., "Anaesthesia for bullectomy. A technique with sponataneous ventilation and extradural blockade," Anaesthesia, 40(10), (1985), 977-980.

Hoes, M. J., "Gamma-hydroxybutyric acid (*) as hypnotic. Clinical and pharmacokinetic evaluation of gamma-hydroxybutyric acid as hypnotic in man," L Encephale, vol. 1, (1980), 93-99.

Laborit, H., "Gamma-Hydroxybutyrate, Succinic Semialdehyde and Sleep," Laboratoire d'Eutonologie, (1973), 257-274.

Ladinsky, et al., "Mediation by the Corticostriatal Input of the In Vivo increase in Rat Striatal Acetylcholine content induced by 2-Choloroadenosine," Biochemical Pharm. vol. 32, No. 19, pp. 2993-2996 (1983).

Ladinsky, H., et al., "Mode of Action of Gamma-Butyrolactone on the Central Cholinergic System, Naunyn-Schmiedeberg's," Arch. Pharmacol., 322, (1983), 42-48.

Lammers, G. J., "Gammahydroxybutyrate and Narcolepsy: A Double-Blind Placebo-Controlled Study," Sleep, 16(3), (1993), 216-220.

Lapierre, O., "The Effect of Gamma-Hydroxybutyrate on Nocturnal and Diurnal Sleep of Normal Subjects: Further Considerations on REM Sleep-Triggering Mechanisms," Sleep, 13, (1990), 24-30.

Lee, C. R., "Evidence for β-Oxidcation of Orally Administered 4-Hydroxybutyrate in Humans," Biochemical Medicine, 17(3), (1977), 284-291.

Lettieri, J., et al., "Improved Pharmacological Activity via Pro-Drug Modification: Comparative Pharmacokinetics of Sodium Y-Hydroxybutyrate and Y-Butyrolactone," Research Communications in Chemical Pathology and Pharmacology, 22(1), (1978), 107-118.

Mamelak, M., "Gammahydroxybutyrate: An Endogenous Regulator of Energy Metabolism," Neuroscience and Biobehavioral Reviews, 13(4), (1989), 187-198.

Mamelak, M., "Sleep-Inducing Effects of Gammahydroxybutyrate," The Lancet, 2(7824), (1973), 328-3.

Mamelak, M., et al., "Treatment of Narcolepsy and Sleep Apnea with Gammahydroxybutyrate: A clinical and polysomnographic case study," Sleep, 4(1), (1981), 105-11.

Mamelak, M., et al., "Treatment of Narcolepsy with y-hydroxybutyrate. A review of Clinical and Sleep Laboratory Findings," 9(1), (1986), 285-90.

Morrison, Robert Thornton, et al., Organic Chemistry, 3rd Edition, (1973), p. 672-677.

Nema, S, et al., "Excipients and Their Use in Injectable Products," PDA J. Pharm. Sci. Technol, 51(4), (1997), 166-171.

Neuman, Ariel, "GHB's Path to Legitimacy: An Administrative and Legislative History of Xyrem," (2004), 1-39.

Ondo, William G. et al., "Sodium Oxybate for Excessive Daytime Sleepiness in Parkinson's Disease: A Polysomnographic Study," Arch. Neural. 2008, 65(10).

Palatini, P., "Dose Dependent Absorption and Elimination of Gamma-Hydroxybutyric Acid in Healthy Volunteers," Eur. J. Clin. Pharmacol., 45(4), (1993), 353-356.

Roth, et al., "y-Butyroiactone and y-Hydroxybutyrie Acid-I, Distribution and Metabolism," Biochemical Pharmacology, 15, (1966), 1333-1348.

Roth, R. H., et al., "y-Butyrolactone and y-Hydroxybutyric acid-II. The Pharmacologically active form," J. Neuropharmacol. 5, (1966), 421-428.

Russel, I. Jon, et al., "Sodium Oxybate Relieves Pain and Improves Function in Fibromyalgia Syndrome," Arthritis. Rheum., 2009, 60: 299-309.

Scharf, Martin B., et al., "The Effects of Sodium Oxybate on Clinical Symptoms and Sleep Patterns in Patients with Fibromyalgia," J. Rheumatol, 2003, 30(5): 1070-1074.

Scharf, M. B., "The Effects and Effectiveness y-Hydroxybutyrate in Patients with Narcolepsy," J. Clin. Psychiatry, 46(6), (1985), 222-225.

Scharf, M. B., et al., "GHB—New Hope for Narcoleptics?," Biol Psychiatry, 26(4), (Aug. 1989), 329-30.

Scrima, et al., "Effect of Gamma-Hydroxybutyrate on a Patient with Obstructive Sleep Apnea," Sleep Research, 16, (1987), 137.

Scrima, et al., "Effect of High Altitude on a Patient with Obstructive Sleep Apnea," Sleep Research, 16, (1987), 427.

(56) References Cited

OTHER PUBLICATIONS

Scrima, et al., "Effects of Gamma-Hydroxybutyrate (GHB) on Narcolepsy-Cataplexy Symptoms and MSLT Results in Male and Female Patients," Association of Professional Sleep Societies, (1988), 251.
Scrima, et al,, "Gamma-Hydroxybutyrate Effects on Catapiexy and Sleep Attacks in Narcoleptics," Sleep Research, 16, (1987), 134.
Scrima, L., et al., "Efficacy of Gamma-Hydroxybutyrate Versus Placebo in Treating Narcolepsy-Cataplexy: Double-Blind Subjective Measures," Biol. Psychiatry, 26(4), (1989), 331-343.
Scrima, L., "The Effects of Y-Hydroxybutyrate on the Sleep of Narcolepsy Patients: A Double-Blind Study," Sleep, 13(6), (1990), 479-490.
Scrima, L., et al., "Narcolepsy," New England J. Med., 324(4), (1991), 270-272.
Series, F., "Effects of Enhancing Slow-Wave Sleep by Gamma-Hydroxybutyrate on Obstructive Sleep Apnea," Am. Rev. Respir. Dis., 145(6), (1992), 1378-1383.
Snead, et al., "Ontogeny of y-Hydroxybutyric Acid, I. Regional Concentration in Developing Rat, Monkey and Human Brain," Brain Res., 227(4), (1981), 579-589.
Snead, O. Carter, "y-Hydroxybutyrate Model of Generalized Absence Seizures: Further Characterization and Comparison with Other Absence Models," Epilepsia, 1988, 29(4): 361-368.
Stock, G., "Increase in brain dopamine after axotomy or treatment with Gammahydroxybutyric acid due to elimination of the nerve impulse flow," Naunyn-Schmiedegerg's Arch. Pharmacol., 278(4), (1973), 347-361.
Strong, A.J., "y-Hydroxybutyric acid and intracranial pressure," The Lancet, (1984), 1304.
Suner, Selim, et al., "Pediatric Gamma Hydroxybutyrate Intoxication," Acad Emerg. Med., vol. 4, (1997), 1041-1045.
Tunnicliff, Godfrey, "Sites of Action of Gamma-Hydroxybutyrate (GHB)—A Neuroactive Drug with Abuse Potential," Clinical Toxicology, 35(6), 581-590 (1997).
Van Den Bogert, A. G., et al., "Placentatransfer of 4-hydroxybutyric acid in man," Anaesthesiology and Intensive Care Medicine, 110,(1978), 55-64.
Vickers, M,D., "Gammahydroxybutyric Acid," Int. Anesth. Clinic, 7(1), (1969), 75-89.
Yamada, Y., "Effect of Butyrolactone and Gamma-Hydroxybutyrate on the EEG and Sleep Cycle in Man," Electroenceph. clin. Neuro physiol., 22, (1967), 558-562.
21 C.F.R. 184, Food and Drug Administration, HHS, (1998), pp. 441-535.
Activase, Physicians Desk Reference (50th ed.), pp. 312, 1058-1061.
Chem Abstract ES302338, SoiFinder®, (1964), 1 pg.
Chemical Abstracts: Seventh Collective Index, vol. 56-65, (1962-1966), 4 pgs.
"HIB-IMUNE," Physicians Desk Reference (41st ed.), (1987), 1095-1096.
"HibVAX," Physicians Desk Reference (41st ed.), (1987), 870.
"Malic Acid," The Handbook of Pharmaceutical Excipients, 2nd Ed., (1994), pp. 285-286, 633.
"Phospholine Iodide," Physicians Desk Reference (50th ed.), (1996), 2784.
"Taxotere," Physicians Desk Reference (51st ed.), (1997), 2204-2207.
United States Pharmacopeial Convention, Inc.: The National Formulary, 23/NF18, (1995), p. 2205.
Restriction Requirement issued Mar. 19, 2001 in U.S. Appl. No. 09/470,570.
Response to Restriction Requirement filed May 3, 2001 in U.S. Appl. No, 09/470,570.
Response to Office Action filed Aug. 10, 2001 in US. Appl. No. 09/470, 570.
Office Action issued Oct. 25, 2001 in U.S. Appl. No. 09/470,570.
Preliminary Amendment filed Nov. 29, 2001 in U.S. Appl. No. 09/470,570.
Office Action issued Dec. 13, 2001 in U.S. Appl. No. 09/470,570.
Response to Office Action filed Mar. 6, 2002 in U.S. Appl. No. 09/470,570.
Notice of Allowance issued Apr. 18, 2002 in U.S. Appl. No. 09/470,570.
Supplementary Notice of Allowance issued Sep. 17, 2002 in U.S. Appl. No. 09/470,570.
Office action issued May 25, 2001 in U.S. Appl. No. 09/470,570.
Notice of allowance issued Mar. 24, 2004 in U.S. Appl. No. 10/194,021.
Preliminary Amendment filed Jul. 11, 2002 in U.S. Appl. No. 10/194,021.
Preliminary Amendment filed May 8, 2004 in U.S. Appl. No. 10/841,709.
Office Action issued Nov. 30, 2006 in U.S. Appl. No. 10/841,709.
Response fiied Feb. 21, 2007 to Office Action issued in U.S. Appl. No. 10/841,709.
Examiner Interview Summary issued Apr. 27, 2007 in U.S. Appl. No. 10/841,709.
Notice of Allowance issued May 25, 2007 in U.S. Appl. No. 10/841,709.
Restriction Requirement issued Jul. 14, 2008 in U.S. Appl. No. 11/777,877.
Response filed Jul. 31, 2008 to Restriction Requirement issued Jul. 14, 2008 in U.S. Appl. No. 11/777,877.
Office Action issued Nov. 6, 2008 in U.S. Appl. No. 11/777,877.
Response filed Apr. 2, 2009 to Office Action issued Nov. 6, 2008 in U.S. Appl. No. 11/777,877.
Final Office Action issued Jul. 10, 2009 in U.S. Appl. No. 11/777,877.
Response filed Jan. 11, 2010 to Final Office Action issued Jul. 10, 2009 in U.S. Appl. No. 11/777,877.
Office Action issued Feb. 3, 2010 in U.S. Appl. No. 11/777,877.
Response filed Jul. 28, 2010 to Office Action issued Feb. 3, 2010 in U.S. Appl. No. 11/777,877.
Notice of Allowance issued Oct. 8, 2010 in U.S. Appl. No. 11/777,877.
Preliminary Amendment filed Jan. 10, 2011 in U.S. Appl. No. 12/913,644.
Office Action issued May 25, 2012 in U.S. Appl. No. 12/913,644.
Supplemental Preliminary Amendment filed Apr. 13, 2012 in U.S. Appl. No. 13/182,324.
Office action issued Jul. 16, 2012 in U.S. Appl. No. 13/182,324.
Response filed Jan. 16, 2013 to Office Action issued Jul. 16, 2012 in U.S. Appl. No. 13/182,324.
Notice of Allowance issued Jan. 30, 2013 in U.S. Appl. No. 13/182,324.
Office Action issued Jun. 28, 2012 in U.S. Appl. No. 13/446,892.
Response filed Aug. 24, 2012 to Office Action issued Ju. 28, 2012 in U.S. Appl. No. 13/446,892.
Notice of Allowance issued Oct. 3, 2012 in U.S. Appl. No. 13/446,892.
Office Action issued Jun. 11, 2012 in U.S. Appl. No 13/446,940.
Response filed Jul. 2, 2012 to Office Action issued Jun. 11, 2012 in U.S. Appl. No. 13/446,940.
Notice of Allowance issued Jul. 16, 2012 in U.S. Appl. No. 131446,940.
Amendment filed Jul. 17, 2012 in U.S. Appl. No. 13/446,940.
Examiner Interview Summary issued Aug. 16, 2012 in U.S. Appl. No. 13/446,940.
Preliminary Amendment filed Feb. 19, 2013 in U.S. Appl. No. 13/685,561.
Supplemental Preliminary Amendment filed Mar. 5, 2013 in U.S. Appl. No. 13/685,561.
Examiner's Report issued Oct. 24, 2003 in Australian Application No, 20590/00.
Search Report issued Jan. 22, 2004 in Australian Application No. 20590/00.
Examiners Report issued May 4, 2004 in Australian Application No. 20590/00.
Response filed Nov. 19, 2004 to Examiner's Report issued May 4, 2004 in Australian Application No. 20590/00.
Office Action issued Jun. 30, 2004 in Canadian Application No. 2,355,293.

(56) References Cited

OTHER PUBLICATIONS

Response filed Oct. 19, 2004 to Office Action issued Jun. 30, 2004 in Canadian Application No. 2,355,293.
Notice of Allowance issued dec. 3, 2004 in Canadian Application No. 2,355,293.
European Search Report issued Apr. 11, 2003 in European Application No. 03075658.9.
Office Action issued Nov. 21, 2001 in European Application No. 99964320.8.
Response filed Feb. 27, 2002 to Office Action issued Nov. 21, 2001 in European Application No. 99964320.8.
Decision to Grant issued Mar. 20, 2003 in European Application No, 99964320.8.
Office Action issued Nov. 19, 2012 in Indian Application No. 2633/KOLNP/2007.
Examination Report issued Jul. 20, 2006 in Indian Application No. IN/PCT/2001/00688.
Response filed Jul. 9, 2007 to Examination Report issued Jul. 20, 2006 in Indian Application No. IN/PCT/2001/00688.
International Search Report issued Jul. 21, 2000 in International Application No. PCT/US99/30740.
Written Opinion issued Oct. 18, 2000 in International Application No. PCT/US99/30740.
Response filed Feb. 16, 2001 to Written Opinion issued Oct. 18, 2000 in International PCT/US99/30740.
International Preliminary Examination Report issued Mar. 26, 2001 in International Application No. PCT/US99/30740.
Notice of Allowance issued Jul. 2, 2006 in Israeli Application No. 143733.
Office Action issued Oct. 5, 2006 in Japanese Application No. 2000-590626.
Response filed Apr. 10, 2007 to Office Action issued Oct. 10, 2006 in Japanese Application No. 2000-590626.
Response filed Jan. 13, 2009 to Final Office Action issued Oct. 14, 2008 in Japanese Application No. 2000-590626.
Notice of Allowance issued Jun. 16, 2009 in Japanese Application No. 2000-590626.
Office Action issued Jan. 17, 2012 Japanese Application No. 2009-028694.
Response filed Jun. 19, 2012 to Office Action issued Jan. 17, 2012 in Japanese Application No. 2009-028694.
Office Action issued Jul. 31, 2012 in Japanese Application No. 2009-028694.
Response filed Jan. 17, 2013 to Office Action issued Jul. 31, 2012 in Japanese Application No. 2009-028694.
Notice of Allowance issued Feb. 5, 2013 in Japanese Application No. 2009-028694.
*Jazz Pharmaceuticals, Inc.* v *Roxane Laboratories, Inc.*, Civil Action No. 12-6761 (ES)(SCM) Identiy of Prior Art Pursuant to Local Patent Rule 3.3(a), (2013).
Markman Opinion, filed. Sep. 14, 2012, in the case of *Jazz Pharmaceuticals, Inc.*, Plaintiff, v. *Roxane Laboratories, Inc.*, Defendant (United States Distric Court for the District of New Jersey, Civil 10-6108 ES.
Order, filed Sep. 14, 2012, in the case of *Jazz Pharmaceuticals, Inc.*, Plaintiff, v. *Roxane Laboratories, Inc.*, Defendant (United States District Court for the District of New Jersery, Civil 10-6108 ES), (Sep. 14, 2012).
Roxane Laboratories, Inc,'s Answer, Affirmative Defenses and Counterclaims to Plaintiffs Complaint, (Jan. 4, 2013).
Roxane Laboratories, Inc.'s Answer, Affirmative Defenses and Counterclaims to Plaintiffs Complaint, (Dec. 29, 2010).
Roxane Laboratories, Inc.'s Answer, Affirmative Defenses and Counterclaims to Plaintiff's Complaint, (Mar. 9, 2011).
Roxane Laboratories, 's Answer, Affirmative Defenses and Counterclaims to Plaintiffs Complaint, (Jun. 1, 2011).
Roxane Laboratories, 's Answer, Affirmative Defenses and Counterclaims to Plaintiffs Complaint, (Nov. 9, 2012).
Roxane Laboratories, Inc.'s Intitial Invalidity and Noninfringement Contentions Pursuant to Local Patent Rule 3.6, (Apr. 14, 2011).
Transcript of a Markman Hearing, dated Apr. 26, 2012, in the case of *Jazz Pharmaceuticals, Inc.*, Plaintiff, v. *Roxane Laboratories, Inc.*, Defendant (United States District Court for the District of New Jersey, Civil 106108 ES), (Apr. 26, 2012).
Preliminary Amendment filed Mar. 24, 2011 in co-pending U.S. Appl. No. 13/071,369.
Notification of Transmittal of the International Search Report and the Written Opinion of the International Searching Authority issued May 17, 2011 in International Application No. PCT/US2011/029802, now WO2011/119839.
Notification Concerning Transmittal of International Preliminary Report on Patentability issued May 19, 2011 in International Application No. PCT/US2009/061312, now WO2010/053691.
Lubrano, et al. "Fibromyalgia in Patients with Irritable Bowel Syndrome. An Association with the Severity of the Intestinal Disorder." Int J Colorectal Dis. Aug. 2001;16(4):211-5.
Moldofsky et al. "A Chronobiologic Theory of Fibromyalgia." J. Muscoloskel. Pain, 1, 49 (1993).
Moldofsky, et al. "Musculoskeletal Symptoms and Non-REM Sleep Disturbance in Patients with 'Fibrositis Syndrome' and Healthy Subjects." Psychosom. Med., 37, 341 (1975).
Outlaw, et al. "Dyspepsia and its Overlap with Irritable Bowel Syndrome." Curr Gastroenterol Rep. Aug. 2006;8(4):266-72.
Remington. The Science and Practice of Pharmacy. 20th Edition, Gennaro, Ed,. Lippincott Williams & Wilkins. Chapter 45 (Oral Solid Dosage Forms) (2000).
Extended European Search Report issued Mar. 23, 2012 in co-pending European Patent Application No. 09825191.1.

\* cited by examiner

IMMEDIATE RELEASE DOSAGE FORMS OF SODIUM OXYBATE

BACKGROUND OF THE INVENTION

Initial interest in the use of sodium oxybate as a potential treatment for narcolepsy arose from observations made during the use of sodium oxybate (known as gamma-hydroxybutyrate in older literature) for anesthesia. Unlike traditional hypnotics, sodium oxybate induces sleep that closely resembles normal, physiologic sleep (Mamelak et al., Biol Psych 1977:12:273-288). Therefore, early investigators administered gamma-hydroxybutyrate (GHB) to patients suffering from disorders of disturbed sleep, including narcolepsy (Broughton et al. in Narcolepsy, NY, N.Y.: Spectrum Publications, Inc. 1976:659-668), where it was found to increase total nocturnal sleep time, decrease nocturnal awakenings and increase Stage 3-4 (slow wave) sleep. Three open-label and two placebo-controlled studies provided a body of evidence demonstrating that improvements in nocturnal sleep were associated with a reduction in cataplexy and improvements in excessive daytime sleepiness (Broughton et al., Can J. Neurol Sci 1979; 6:1-6, and Broughton et al., Can J. Neurol Sci 1980; 7:23-30)

Scharf et al. conducted an open-label study to evaluate the effects of GHB on the sleep patterns and symptoms of non-narcoleptic patients with fibromyalgia (Scharf et al., J Rheumatol 1998; 25: 1986-1990). Eleven patients with previously confirmed diagnosis of fibromyalgia who reported at least a 3-month history of widespread musculoskeletal pain in all body quadrants and tenderness in a least 5 specific trigger point sites participated in the study. Results showed that patients reported significant improvements in the subjective assessments of their levels of pain and fatigue over all 4 weeks of GHB treatment as compared to baseline, as well as a significant improvement in their estimates of overall wellness before and after GHB treatment.

WO 2006/053186 to Frucht describes an open label study of 5 patients with hyperkinetic movement disorders including ethanol responsive myoclonus and essential tremor. Sodium oxybate was reported to produce dose-dependent improvements in blinded ratings of ethanol responsive myoclonus and tremor and was said to be tolerated at doses that provided clinical benefit.

Xyrem® sodium oxybate oral solution, the FDA approved treatment for cataplexy and excessive daytime sleepiness associated with narcolepsy, contains 500 mg sodium oxybate/ml water, adjusted to pH=7.5 with malic acid. In man, the plasma half-life of sodium oxybate given orally is about 45 minutes and doses of 2.25 grams to 4.5 grams induce about 2 to 3 hours of sleep (See, L. Borgen et al., *J. Clin. Pharmacol.*, 40, 1053 (2000)). For optimal clinical effectiveness in narcolepsy, sodium oxybate must be given twice during the night, and is administered as an aqueous solution. For each dose, a measured amount of the oral solution must be removed from the primary container and transferred to a separate container where it is diluted with water before administration. The second dose is prepared at bedtime and stored for administration in the middle of the night. This regimen is cumbersome and prone to errors in the preparation of the individual doses. For this reason, a more convenient unit dosage form of the drug would be clinically advantageous. Sodium oxybate is highly water-soluble, hygroscopic and strongly alkaline. Paradoxically, despite its high water solubility, it forms a gel when dissolved in water. These properties, along with the large amount of the drug that is required to achieve the clinical effect, present challenges in preparing solid unit dosage forms that are designed for immediate release of the sodium oxybate into the gastrointestinal tract of the user.

L. Liang et al. (published U.S. patent application US 2006/0210630A1) discloses administration of gamma-hydroxybutyric acid using an immediate release component and a delayed/controlled release component. The immediate release component is disclosed to be an aqueous solution, or a "solid pellet, bead or mini tablet." While the pellets disclosed in Example 1 comprise as much as 80-90 wt-% sodium gamma-hydroxybutyrate, they are the immediate release portion of the controlled release dosage form and are not formed into a compressed tablet. They are added to other forms of sodium oxybate to prepare controlled release dosage forms.

A continuing need exists for solid immediate release dosage forms of sodium oxybate that can deliver therapeutically effective amounts of sodium oxybate following in vivo administration and which have pharmacokinetic profiles similar to that of the oral solution.

SUMMARY OF THE INVENTION

The present invention provides a pharmaceutical composition, presented as a solid unit dosage form adapted for oral administration of a therapeutic dose of sodium oxybate. The preferred unit dosage form is a tablet comprising a relatively high weight-percentage of sodium oxybate, in combination with a relatively small weight-percentage of total excipients. This permits the tablets to contain/deliver a pharmaceutically effective amount, e.g., about 0.5-1.5 g of sodium oxybate in each tablet with a delivery profile similar to that of the liquid form. The tablets are bioequivalent to the liquid form.

In one aspect the invention is a compressed tablet of sodium oxybate for oral delivery of 0.5-1.25 g of sodium oxybate comprising at least 50 wt % sodium oxybate; 1-10 wt % compression aid; and 1-50% binder; wherein the tablet is bioequivalent to sodium oxybate oral solution.

According to one embodiment, the tablet may be coated to 1-10 wt % gain with a film coating. The tablet may comprise 70-90 wt % sodium oxybate, or 80-90 wt % sodium oxybate. The tablet need not contain a super-disintegrant. The tablet may further comprise 0.1-10 wt % of a surfactant.

In another aspect, the invention is directed to an immediate release unit dosage form comprising an about 0.5-1.5 g tablet comprising about 50-95 wt-% sodium oxybate; about 2.5-7.5 wt-% microcrystalline cellulose and about 0.25-2.5 wt-% surfactant, wherein at least 90% of the sodium oxybate is released from the tablet within one hour from exposure of the tablet to an aqueous medium.

In a particular embodiment, the unit dosage form is coated with a water resistant coating. Further, the surfactant may be an ionic or nonionic surfactant. The dosage form may further comprise a minor but effective amount of at least one of a second binder, a disintegrant, a glidant and a lubricant and also may comprise 0.5-5 wt-% polyvinylpyrrolidone, 2.5-7.5 wt-% pregelatinized starch, 0.1-2.0 wt-% silicon dioxide and/or magnesium stearate.

In still another aspect, the invention is directed to a therapeutic method for treating a human afflicted with a condition treatable with sodium oxybate by orally administering to said human an effective amount of one or more of the unit dosage forms or tablets described above. The conditions may include narcolepsy, a movement disorder (such as restless leg syndrome or essential tremor), fibromyalgia or chronic fatigue syndrome.

Another aspect of the invention is a method for preparing the tablets and dosage forms described above by granulating a water-free composition comprising the sodium oxybate, the compression and the binder; and compressing the granulated composition to yield said tablet. The tablet may be coated with a water resistant coating that may comprise PVA and lecithin.

In a further aspect the invention is a compressed tablet of an oxybate salt for oral delivery of 0.5-1.25 g of oxybate salt comprising at least 50 wt % oxybate salt; 5-10 wt % compression aid; and 1-50% binder; wherein the tablet is bioequivalent to sodium oxybate oral solution. The oxybate salt may be selected from the group consisting of potassium oxybate, calcium oxybate, lithium oxybate and magnesium oxybate.

BRIEF DESCRIPTIONS OF THE FIGURES

DETAILED DESCRIPTION OF THE INVENTION

Figure 1:
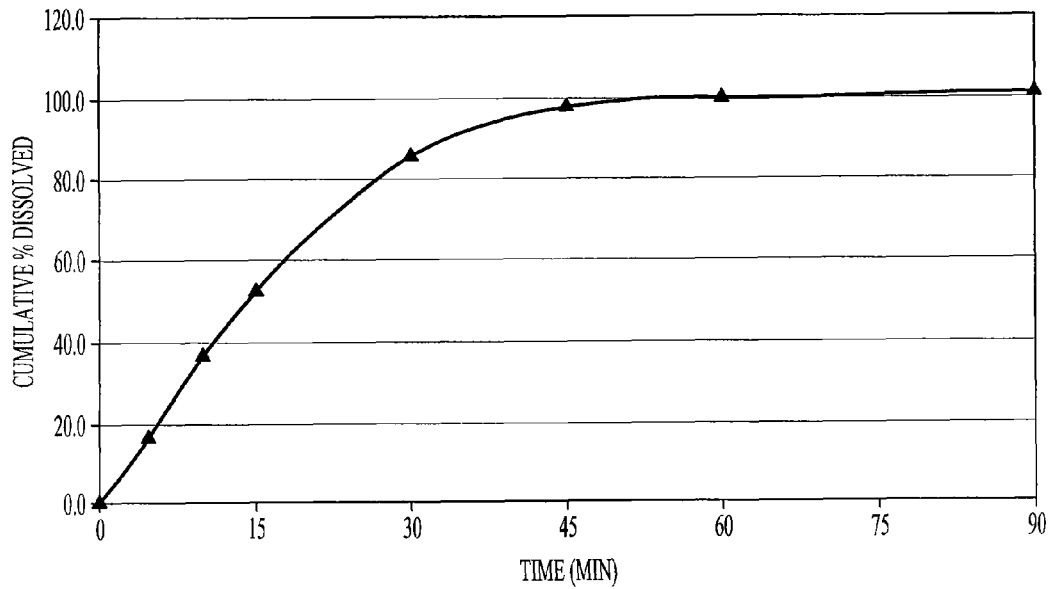
FIG. 1 is a graph depicting the dissolution curve of an immediate release sodium oxybate tablet of the invention.

Administration of sodium oxybate in solid form presents several challenges. The amount of drug taken by the patient for each dose is high, generally at least 1.5 grams and as high as 4.5 grams. Patients treated with sodium oxybate may have difficulty taking solid medications by mouth either because they have disease states that make handling and swallowing difficult or because they must take the medication upon being awakened in the middle of the night. The situation is exacerbated by the large quantity of drug that is administered in each dose. Accordingly, it is desirable to keep the size of the tablet as small as possible while incorporating the largest amount of active ingredient. In addition, the tablet must dissolve quickly in order to be bioequivalent to the existing Xyrem oral solution, without high levels of excipients to speed dissolution.

Therefore, according to the invention, the immediate release sodium oxybate composition will comprise a therapeutically effective amount of sodium oxybate or an alternative salt thereof. The structure of sodium oxybate is given below as formula (Ia):

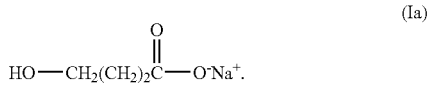

(Ia)

Alternative salts useful in the present invention include compounds of formula (I):

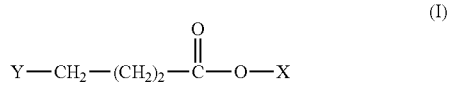

(I)

wherein X is a pharmaceutically-acceptable cation and may be selected from the group consisting of potassium, calcium, lithium and magnesium and Y is OH. Sodium gamma-hydroxybutyrate (GHB) is currently available from Jazz Pharmaceuticals, Inc. as Xyrem® oral solution.

A "delivery rate" refers to the quantity of sodium oxybate released in vivo from a composition (tablet or dosage form) according to the invention per unit time, e.g., milligrams of sodium oxybate released per unit time.

By "immediate release" is intended a composition that releases sodium oxybate substantially completely into the gastrointestinal tract of the user within a period of less than an hour, usually between about 0.1 and about 1 hour and less than about 0.75 hours from ingestion. Such a delivery rate allows the drug to be absorbed by the gastrointestinal tract in a manner that is bioequivalent to the oral solution. The rapid release of sodium oxybate from the tablet is especially important because following delivery of the oral solution, peak plasma concentration of sodium oxybate occurs within an hour. Such rapid absorption could only occur if the tablet dissolves in the upper portion the gastrointestinal tract.

A "dissolution rate" refers to the quantity of drug released in vitro from a dosage form per unit time into a release medium. In vitro dissolution rates in the studies described herein were performed on dosage forms placed in a USP Type II bath containing water which is stirred while maintained at a constant temperature of 37° C. Aliquots of the dissolution media were injected into a chromatographic system to quantify the amounts of drug dissolved during each testing interval.

By "bioavailability" as used herein is intended the estimated area under the curve, or AUC of the active drug in systemic circulation after oral administration with a dosage form according to the invention compared with the AUC of the active drug in systemic circulation after oral administration of Xyrem, sodium oxybate oral solution. The AUC is affected by the extent to which the drug is absorbed in the GI tract. In the case of sodium oxybate, absorption is greatest in the upper GI tract, so that a solid dosage form must dissolve quickly in order to be bioequivalent to the oral solution.

Products are considered to be "bioequivalent" if the relative mean $C_{max}$, $AUC_{(0-t)}$ and $AUC_{(0-\infty)}$ of the test product to reference product is within 80% to 125%.

A "compressed" tablet is one in which the drug and the excipients are bonded together sufficiently that they exhibit minimum friability (less than 1%) when tumbled in a testing apparatus designed for that purpose.

By "sodium oxybate oral solution" is intended the product currently known as Xyrem, a solution that contains 500 mg sodium oxybate/ml water, adjusted to pH=7.5 with malic acid.

The term "$AUC_{0-t}$" means the area under the plasma concentration curve from time 0 to time t.

The term "$AUC_{0-\infty}$" or "$AUC_{0-inf}$" means the area under the plasma concentration time curve from time 0 to infinity.

By "$C_{max}$" is intended the maximum plasma concentration of sodium oxybate. The $C_{max}$ of a 3 gram dose of immediate release tablets is between 10 and 200 μg/mL, often between 20 and 120 μg/mL. Such profiles are especially desirable for diseases such as narcolepsy, cataplexy, movement disorders such as essential tremor and restless leg syndrome, fibromyalgia and chronic fatigue syndrome.

By "$t_{max}$" is intended the time to maximum plasma concentration and for sodium oxybate is between 0.5 and 2.5 hours, often between 0.5 and 1.5 hours and "$t_{1/2}$" is intended the time to 50% plasma concentration and for sodium oxybate is between 0.4 and 0.9 hours, often between 0.5 and 0.7 hours.

The apparent elimination rate constant is "$\lambda_z$" and may be between 0.5 and 2.5 hours$^{-1}$.

By "oxybate salt" is intended a compound of formula I wherein X is a pharmaceutically-acceptable cation and may be selected from the group consisting of sodium, potassium, calcium, lithium and magnesium and Y is OH.

By "sodium oxybate" is intended a compound of formula Ia.

The pharmaceutical immediate release compositions suitable for oral administration comprise solid unit dosage forms or "tablets" which can deliver a therapeutically effective dose of sodium oxybate upon ingestion thereof by the patient of one or more of said tablets, each of which can provide a dosage of about 0.5-1.5 g of sodium oxybate (or equivalent thereof). Additionally, the tablets could be shaped and scored to make them easier to swallow.

Examples of fillers/compression aids useful in said tablets include: lactose, calcium carbonate, calcium sulfate, compressible sugars, dextrates, dextrin, dextrose, kaolin, magnesium carbonate, magnesium oxide, maltodextrin, mannitol, microcrystalline cellulose, powdered cellulose, and/or sucrose.

Examples of binders useful in said tablets include povidone and pregelatinized starch. Other examples of binders include dextrin, gelatin, hydroxypropyl methylcellulose, maltodextrin, starch, and zein. Further examples of binders include but are not limited to: acacia, alginic acid, carbomers (cross-linked polyacrylates), polymethacrylates, carboxymethylcellulose sodium, ethylcellulose, guar gum, hydrogenated vegetable oil (type 1), hydroxyethyl cellulose, hydroxypropyl cellulose, methylcellulose, magnesium aluminum silicate, and/or sodium alginate.

Surfactant/wetting agent concentrations can be varied between 0.1 and 10 wt-% to complement the drug amount in said tablets. Examples of surfactants/wetting agents comprise ionic and nonionic surfactants. Examples of non-ionic surfactants include polyoxyethyelene alkyl ethers, polyoxyethylene stearates, and/or poloxamers. Examples of ionic surfactants include but are not limited to sodium lauryl sulfate, docusate sodium (dioctyl sulfosuccinate sodium salt), benzalkonium chloride, benzethonium chloride, and cetrimide (alkyltrimethylammonium bromide, predominantly $C_{14}$-alkyl). Further examples of non-ionic surfactants include but are not limited to polysorbate, sorbitan esters, and glyceryl monooleate.

Glidant agent concentrations in said tablets can be varied between 0.1 and 5 wt-% to complement the drug amount. Examples of glidant agents are calcium phosphate dibasic, calcium silicate, colloidal silicon dioxide, magnesium silicate, magnesium trisilicate, silicon dioxide, starch, talc or combinations thereof.

Lubricant concentrations in said tablets can be varied from 0.1 to 5 wt-%. Examples of useful lubricants include: calcium stearate, hydrogenated castor oil, hydrogenated vegetable oil, light mineral oil, magnesium stearate, mineral oil, polyethylene glycol, sodium benzoate, sodium stearyl fumarate, stearic acid, and zinc stearate.

Protection of the sodium oxybate composition from water during storage may also be provided or enhanced by coating the tablet with a continuous coating of a substantially water soluble or insoluble polymer. Useful water-insoluble or water-resistant coating polymers include ethyl cellulose and polyvinyl acetates. Further water-insoluble or water resistant coating polymers include polyacrylates, polymethacrylates or the like. Suitable water-soluble polymers include polyvinyl alcohol and HPMC. Further suitable water-soluble polymers include PVP, HPC, HPEC, PEG, HEC and the like.

For example, the present tablet is a solid body of about 750 mg-1.5 g of a composition comprising about 50-95 wt-%, preferably about 70-92.5 wt-% sodium oxybate, preferably about 75-90 wt-% sodium oxybate. The present tablets also comprise about 2.5-7.5 wt-% of one or more microcrystalline cellulose(s). These materials, which can include Avicel® PH 101 and SMCC 50, function as direct compression binders.

The present tablets also preferably comprise about 0.25-2.5 wt-% surfactant, preferably an anionic surfactant such as sodium lauryl sulfate or docusate sodium. Nonionic surfactants such as a poloxamer, a polysorbate, glyceryl mono-fatty acid esters, polyoxyethylene fatty acid esters and/or polyoxyethylene ethers of fatty alcohols; and cationic surfactants such as benzalkonium chlorides, benzethonium chlorides and cetrimide, can also be used. Normally, surfactants are added to formulations of drugs that are poorly water soluble in order to wet the surface of the drug particles. They generally have little or no effect on the dissolution of water soluble drugs like sodium oxybate. However, it was surprising that the addition of small amounts of surfactant to the tablets produced substantially faster dissolution, although addition of surfactant to the dissolution media, in equivalent or higher amounts did not produce the same effect.

The present tablets can also contain minor but effective amounts of other compression aids, fillers, binders, disintegrants, glidants and/or lubricants. For example, the present tablets can preferably contain about 2.5-15 wt-%, e.g., about 3-10 wt-% of other binder(s), disintegrant(s), glidant(s), or a combination thereof, including polyvinylpyrrolidone, pregelatinized starch, lactose, dibasic calcium phosphate and a compressible sugar such as sorbitol.

Preferably, the secondary binders comprise a mixture of about 0.5-5 wt-% polyvinylpyrrolidone (povidone) and about 2.5-7.5 wt-% pregelatinized starch. The glidant/disintegrant is preferably 0.1-0.75 wt-% silicon dioxide (e.g., Cab-O-Sil® MPS) and the lubricant is a fatty acid salt such as magnesium stearate or stearic acid. The present weight percentages are weight percentages of the ingredients in an uncoated capsule.

Because sodium oxybate is hygroscopic, it is preferred to coat the present tablet of the invention with a moisture-resistant coating such as a polyvinyl alcohol/lecithin-based coating (Opadry® AMB) or a hypromellose, microcrystalline cellulose, stearic acid coating (Sepifilm® LP 014). The coating can make up about 1-5 wt-% of the weight of the coated capsule, e.g., about 1.25-5.5 wt-% of the uncoated capsule.

Unexpectedly, the present tablets do not require the use of a high-performance disintegrant, such as a modified cellulosic disintegrant, e.g., croscarmellose sodium, (a cross-linked carboxymethyl cellulose) to achieve in vivo bioavailability equivalent to that achieved by the Xyrem® sodium oxybate oral solution. Typically, such high performance disintegrants are added at about 5-10 wt-% of immediate release compositions. In this case, the drug forms a gel upon exposure to water, so despite the high solubility of sodium oxybate, unique issues arise when attempting to produce a solid oral dosage form that will rapidly disintegrate. A "superdisintegrant' is usually added, but with this gel forming drug, such an additive would not aid in disintegration. Instead, a surfactant was added to the mixture prior to roller compaction so that it is intra-granularly incorporated. Such intra-granular incorporation speeds up dispersion of the gelled drug so that the tablet dissolves faster. Further, it allows water to enter the dosage form and aid in its disintegration, a phenomenon that would be expected with a hydrophilic drug, rather than a hydrophobic one such as sodium oxybate.

Controlled release formulations of gamma-hydroxybutyrate comprising a delayed or controlled release component and an immediate release component are described in U.S. 2006/0210630 A1. Pellets are formed from compositions that typically comprise 10-50 wt-% of one or more microcrystalline celluloses, in combination with 40-90 wt-% sodium oxybate. The pellets are formed by adding 10-20 wt-% water during the granulation and extrusion process of the composition that yields the GHB pellets. The pellets are then dispersed in a solution of GHB.

The present immediate release dosage form is adapted for oral administration, so as to attain and maintain a therapeutic level of sodium oxybate over a preselected interval. The tablet contains a relatively large percentage and absolute amount of sodium oxybate and so is expected to improve patient compliance and convenience, by replacing the need to ingest large amounts of liquids or liquid/solid suspensions. One or more immediate release tablets can be administered, by oral ingestion, e.g., closely spaced, in order to provide a therapeutically effective dose of sodium oxybate to the subject in a relatively short period of time. For example, disintegration of a 500 mg-1.0 g tablet can provide about 95-100% of the oxybate to the subject in about 30-60 minutes.

The present invention also provides therapeutic methods to treat conditions amenable to treatment by sodium oxybate, such as those discussed hereinabove, by administering an effective amount of one or more dosage forms of the invention.

The present dosage forms can be administered to treat a human afflicted with narcolepsy to reduce cataplexy and/or daytime sleepiness.

The present dosage forms can be administered to humans, particularly in the elderly (>50 years old), to improve the quality of sleep, or in conditions in which an increase in growth hormone levels in vivo is desired.

The present dosage forms can also be used to treat fibromyalgia or chronic fatigue syndrome, e.g., to alleviate at least one symptom of fibromyalgia or chronic fatigue syndrome. See, U.S. Pat. No. 5,990,162.

The dosage forms of the present invention can also be provided as a kit comprising, separately packaged, a container comprising a plurality of the immediate release tablets of the invention, which tablets can be individually packaged, as in foil envelopes or in a blister pack. The tablets can be packaged in many conformations with or without dessicants or other materials to prevent ingress of water. Instruction materials or means, such as printed labeling, can also be included for their administration, e.g., sequentially over a preselected time period and/or at preselected intervals, to yield the desired levels of sodium oxybate in vivo for preselected periods of time, to treat a preselected condition.

The present invention also provides a particulate composition, such as granules, that can be tabletted by compression without the addition of exogenous water before, during or after the tabletting process. This can assist in preserving the bioactivity of the sodium oxybate during the tablet preparation process.

A daily dose of about 1-1000 mg/kg of sodium oxybate or other oxybate salt such as a compound of formula (I) can be administered to accomplish the therapeutic results disclosed herein. For example, a daily dosage of about 0.5-20 g of the sodium oxybate or of a compound of formula (I) can be administered, preferably about 1-15 g, in single or divided doses. For example, useful dosages and modes of administration are disclosed in U.S. Pat. Nos. 5,990,162 and 6,472,432. Methods to extrapolate from dosages found to be effective in laboratory animals such as mice, to doses effective in humans are known to the art. See U.S. Pat. No. 5,294,430, or 4,939,949.

As noted herein above, the dosage forms of the present invention may be useful in the treatment of a variety of conditions amenable to treatment by sodium oxybate, such as narcolepsy to reduce cataplexy and/or daytime sleepiness, to improve the quality of sleep, or in conditions in which an increase in growth hormone levels in vivo is desired, and to treat fibromyalgia or chronic fatigue syndrome. The present dosage forms may be used to treat a host of other indications including drug and alcohol abuse, anxiety, cerebrovascular diseases, central nervous system disorders, neurological disorders including Parkinson's Disease and Alzheimer Disease, Multiple Sclerosis, autism, depression, inflammatory disorders, including those of the bowel, such as irritable bowel disorder, regional illitis and ulcerative colitis, autoimmune inflammatory disorders, certain endocrine disturbances and diabetes.

The present dosage forms may also be administered for the purpose of tissue protection including protection following hypoxia/anoxia such as in stroke, organ transplantation, organ preservation, myocardial infarction or ischemia, reperfusion injury, protection following chemotherapy, radiation, progeria, or an increased level of intracranial pressure, e.g. due to head trauma. The present dosage forms can also be used to treat other pathologies believed to be caused or exacerbated by lipid peroxidation and/or free radicals, such as pathologies associated with oxidative stress, including normal aging. See Patent Publication US 2004/0092455 A1. The present dosage forms may also be used to treat movement disorders including restless leg syndrome, myoclonus, dystonia and/or essential tremor. See Frucht et al, *Movement Disorders*, 20(10), 1330 (2005).

The invention will be further described by reference to the following detailed examples.

Example 1

Immediate Release Sodium Oxybate Tablets

This example provides 3 formulations of compressed tablets of sodium oxybate which have greater than 70% drug loading. The tablets were prepared using roller compaction as the manufacturing method for the granulation. The composition of the tablets is summarized on Table 1, below:

TABLE 1

| Ingredient(s) | % (w/w) | Qty/Unit (mg) |
|---|---|---|
| Formulation A | | |
| Sodium Oxybate | 71.4 | 750.0 |
| Microcrystalline Cellulose (Avicel PH 101) | 12.1 | 126.7 |
| Povidone (PVP K-17) | 2.00 | 21.0 |
| Croscarmellose Sodium NF/EP (Ac-Di-Sol SD-711) | 12.0 | 126.0 |
| Colloidal Silicon Dioxide (Cab-O-Sil MP5) | 0.50 | 5.3 |
| Sodium Lauryl Sulfate | 1.00 | 10.5 |
| Magnesium Stearate, NF (vegetable grade) (0.7% intragranular, 0.5% extragranular) | 1.0 | 10.5 |
| Formulation B | | |
| Sodium Oxybate | 78.9 | 750.0 |
| Microcrystalline Cellulose (Avicel PH 101) | 5.9 | 55.6 |
| Povidone (PVP K-17) | 2.0 | 19.0 |
| Pregelatinized Starch (Starch 1500) | 5.0 | 47.5 |
| Colloidal Silicon Dioxide (Cab-O-Sil MP5) | 0.5 | 4.8 |
| Magnesium Stearate, NF (vegetable grade) (0.7% intragranular, 0.5% extragranular) | 1.2 | 11.4 |
| Croscarmellose Sodium, NF/EP (Ac-Di-Sol SD-711) | 6.5 | 61.8 |

TABLE 1-continued

| Ingredient(s) | % (w/w) | Qty/Unit (mg) |
|---|---|---|
| Formulation C | | |
| Sodium Oxybate | 84.46 | 750.0 |
| Microcrystalline Cellulose (Avicel PH 101) | 5.84 | 51.9 |
| Povidone (PVP K-17) | 2.00 | 17.8 |
| Pregelatinized Starch (Starch 1500) | 5.00 | 44.4 |
| Colloidal Silicon Dioxide (Cab-O-Sil MP5) | 0.50 | 4.4 |
| Sodium Lauryl Sulfate | 1.00 | 8.9 |
| Magnesium Stearate, NF (vegetable grade) (0.7% intragranular, 0.5% extragranular) | 1.20 | 10.7 |

To prepare a one kilogram batch of the tablets in Table 1, all the ingredients were hand-screened through a 20 mesh screen. All of the ingredients except the magnesium stearate, were transferred to a blender, and mixed for five minutes. A intragranular portion of the magnesium stearate (6.2 g) was added to the blender and mixing continued for 3 minutes. The material was passed through a roller compactor to make ribbons with thickness of 1.4±0.5 mm, without added water. The ribbons were milled and then granulated with a 16-mesh screen. The granulate was added to the blender and mixed for 5 minutes. The remaining magnesium stearate (4.5 g) was added to the blend, and mixed for 3 minutes. The blend was compressed into tablets on a standard tablet press to the following specifications: (a) Weight 888 mg; (b) Hardness: 15 kP hardness; (c) Disintegration time: NMT 15 min.; and (d) Friability: NMT 1.0% after 100 drops (n=10).

To coat the tablets of Formulation C, a 10% Opadry® AMB dispersion was prepared in ethanol/water. The ethanol and water was charged into a stainless steel pot and mixed for 3 minutes using an overhead mixer. Opadry® AMB Blue was slowly added into the vortex of the stirred liquid. The stirring speed was reduced and stirring continued for ≥30 minutes. The tablets were placed in the coating pan and preheated to 45° C. The tablets were coated to a 4% weight gain (35.5 mg/unit).

Example 2

Bioavailability and Bioequivalence of Sodium Oxybate Tablets

A Phase I, three-way, open-label, randomized single-dose crossover study of Formulation A (4.5 grams of Formulation A given as 6 tablets: Treatment A), Formulation B (4.5 grams of Formulation B given as 6 tablets: Treatment B), and Xyrem (4.5 grams of sodium oxybate oral solution: Treatment C). Following a 1 to 21-day screening period, the study duration for each subject was approximately 7 days, Period 1 comprising Days 1 to 2, Period 2 comprising Days 3 to 4, and Period 3 Days 5 to 6. A 2-day washout period (dosing on the morning of the first day followed by a I day washout) separated the Treatments A, B and C.

Single doses (4.5 g, given as 6×750 mg tablets) of sodium oxybate solid dosage Formulations A and B and Single doses (4.5 g) of sodium oxybate oral solution (Xyrem) were administered orally in the morning following a 10-hour fast, with subjects remaining fasted for a further 4 hours after dosing. The PK profile for sodium oxybate was evaluated over an 8-hour period, based on blood samples (5 mL) collected pre-dose; at 10, 20, 30, 45, 60 and 75 minutes post-dose; and at 1.5, 2, 2.5, 3, 3.5, 4, 4.5, 5, 6, 7 and 8 hours post-dose following each treatment. The PK parameters calculated for plasma sodium oxybate concentrations included: the area under the plasma concentration time curve from time 0 to time t of the last quantifiable concentration [$AUC_{0-t}$], and area under the plasma concentration time curve from time 0 to infinity[$AUC_{0-\infty}$], maximum plasma concentration of sodium oxybate ($C_{max}$), time to maximum plasma concentration ($t_{max}$), the apparent elimination rate constant ($\lambda_z$) and half-life ($t_{1/2}$) and the relative bioavailability for solid dosage Formulations A and B versus Xyrem.

The relative bioavailability of Treatments A and B versus Treatment C (Xyrem) based on AUC values were 98% and 100%, respectively. All treatments were found to be bioequivalent with regard to $C_{max}$ and total exposure AUC after oral administration of sodium oxybate.

TABLE 2

Summary of Mean (SD) Sodium Oxybate Pharmacokinetic Parameters

| PK Parameter | Units | | Treatment A (Test) | Treatment B (Test) | Treatment C (Reference) |
|---|---|---|---|---|---|
| $C_{max}$ | (µg/mL) | Mean | 129 | 135 | 143 |
| | | SD | 37.6 | 37.2 | 29.2 |
| | | Geometric Mean | 123 | 131 | 140 |
| | | Geometric SD | 1.39 | 1.32 | 1.23 |
| $t_{max}$ | (hr) | Median | 1.00 | 1.00 | 0.750 |
| | | Min, Max | 0.750, 2.50 | 0.500, 2.50 | 0.500, 1.50 |
| $AUC_{0-t}$ | (µg * hr/mL) | Mean | 297 | 303 | 298 |
| | | SD | 104 | 112 | 96.3 |
| | | Geometric Mean | 275 | 280 | 281 |
| | | Geometric SD | 1.53 | 1.53 | 1.45 |
| $AUC_{0-inf}$ | (µg * hr/mL) | Mean | 298 | 304 | 300 |
| | | SD | 104 | 112 | 96.6 |
| | | Geometric Mean | 277 | 282 | 283 |
| | | Geometric SD | 1.53 | 1.53 | 1.45 |
| $t_{1/2}$ | (hr) | Mean | 0.584 | 0.561 | 0.646 |
| | | SD | 0.196 | 0.139 | 0.245 |
| $\lambda_z$ | (hr$^{-1}$) | Mean | 1.30 | 1.32 | 1.19 |
| | | SD | 0.414 | 0.398 | 0.345 |

Example 3

Dissolution Profiles of Sodium Oxybate Tablets

Figure 2:
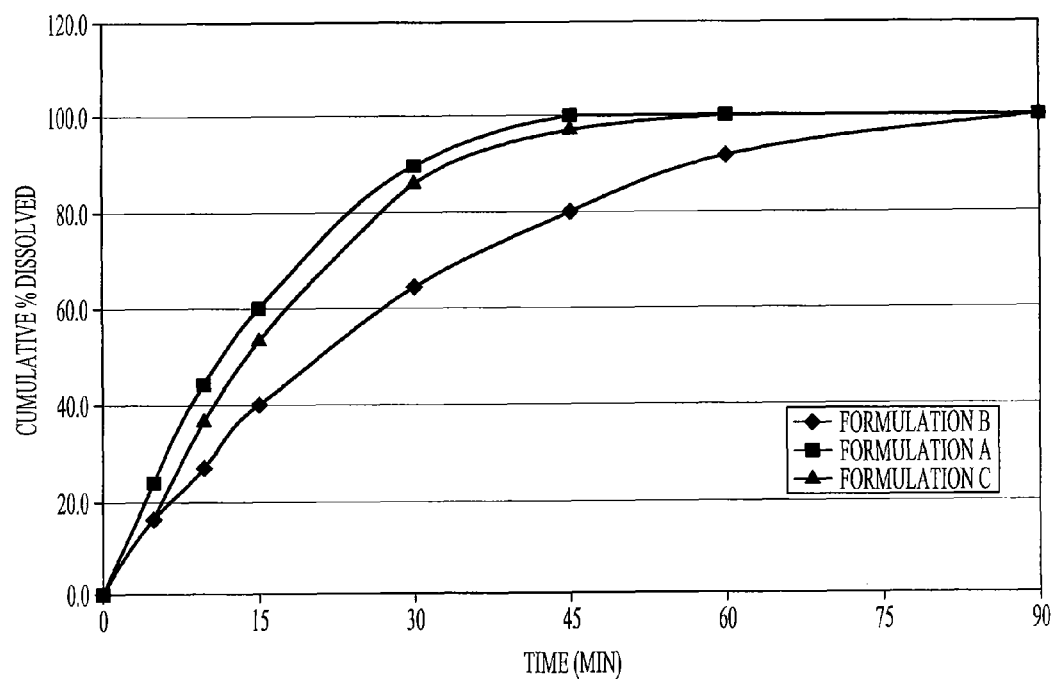
FIG. 2 is a graph depicting the dissolution curves of three immediate release sodium oxybate tablets according to the invention.

FIG. 1 shows the dissolution profile of one embodiment of the invention. The dosage form described in Example 1 as Formulation C has an immediate release profile. The immediate release tablets release sodium oxybate in less than 1 hour. This release profile was intermediate between the two dissolution curves of immediate release compositions described in Example 1 (Formulations A and B—see FIG. 2) which was shown to be bioequivalent to Xyrem® solution (see Example 2), thus demonstrating that this composition is also bioequivalent to Xyrem® solution.

Example 4

Dissolution Profiles of Sodium Oxybate Tablets

| Formulation D | | |
|---|---|---|
| Ingredient(s) | % (w/w) | Qty/Unit (mg) |
| Sodium Oxybate | 78.95 | 750.0 |
| Microcrystalline Cellulose (Avicel PH 101) | 4.85 | 46.1 |
| Povidone (PVP K-17) | 2.00 | 19.0 |
| Pregelatinized Starch (Starch 1500) | 5.00 | 47.5 |
| Croscarmellose Sodium NF/EP (Ac-Di-Sol SD-711) | 6.50 | 61.8 |
| Poloxamer 188 | 1.00 | 9.5 |
| Colloidal Silicon Dioxide (Cab-O-Sil MP5) | 0.50 | 4.8 |
| Magnesium Stearate, NF (vegetable grade) | 1.20 | 11.4 |

Figure 3:
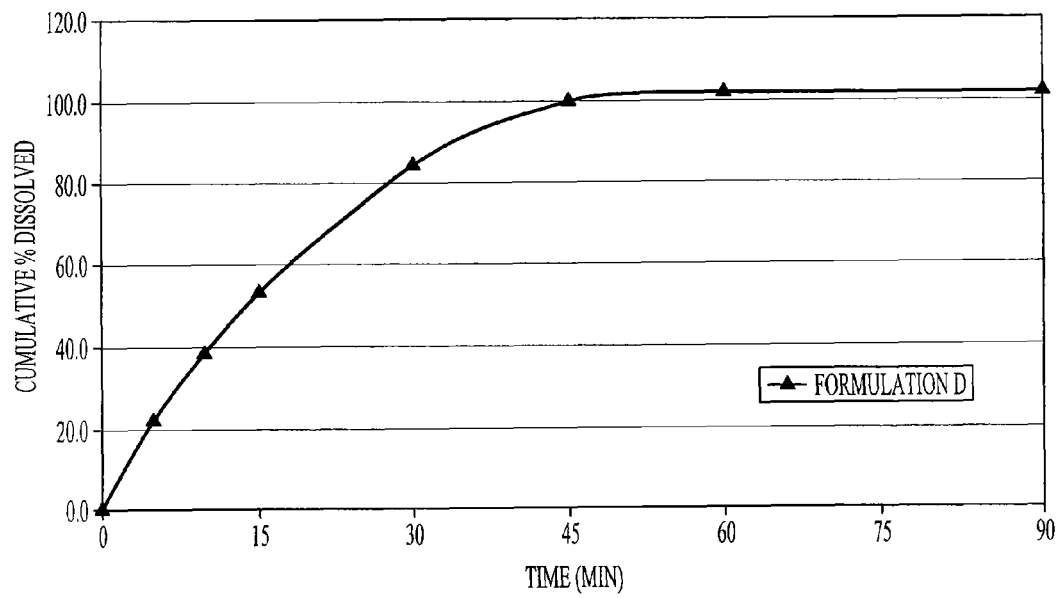
FIG. 3 is a graph depicting the dissolution curve of a further immediate release sodium oxybate tablet according to the invention.
Figure 4:
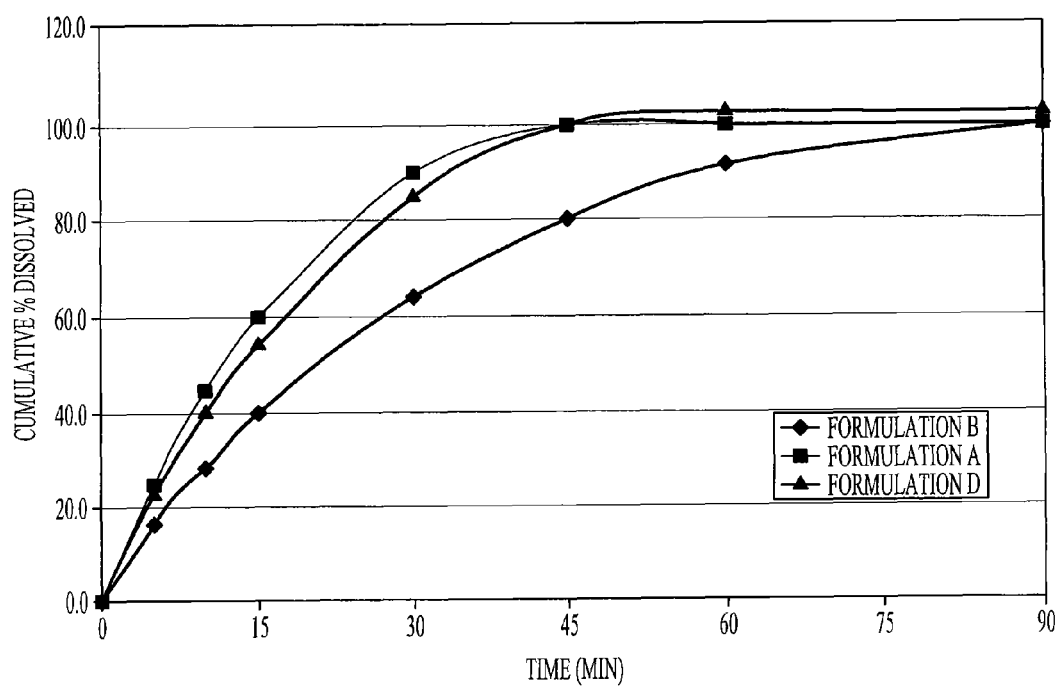
FIG. 4 is a graph depicting the dissolution curves of three immediate release sodium oxybate tablets according to the invention.

A one kilogram batch of tablets of Formulation D were prepared as described in Example 1 except using poloxamer as a surfactant rather than sodium lauryl sulfate. FIG. 3 shows the dissolution profile of Formulation D. The tablets have an immediate release profile and deliver sodium oxybate in less than 1 hour. This release profile was intermediate between the two dissolution curves of immediate release compositions described in Example 1 (Formulations A and B—see FIG. 4) which were shown to be bioequivalent to Xyrem® solution (see Example 2), thus demonstrating that this composition is also bioequivalent to Xyrem® solution.

All publications, patents, and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A compressed tablet of sodium oxybate for oral delivery of 0.5-1.25 g of sodium oxybate comprising 80-95 wt % sodium oxybate; 5-10 wt % compression aid; and 1-50% binder; wherein the tablet is bioequivalent to sodium oxybate oral solution.

2. The compressed tablet of claim 1, wherein the tablet is coated to 1-10 wt % gain with a film coating.

3. The compressed tablet of claim 1, wherein the tablet comprises 80-90 wt % sodium oxybate.

4. The compressed tablet of claim 1, wherein the tablet does not contain a super-disintegrant.

5. The compressed tablet of claim 1, wherein the tablet further comprises 0.1-10 wt % of a surfactant.

6. An immediate release unit dosage form comprising an about 0.5-1.5 g compressed tablet comprising 80-95 wt-% sodium oxybate; about 2.5-7.5 wt-% microcrystalline cellulose and about 0.25-2.5 wt-% surfactant, wherein at least 90% of the sodium oxybate is released from the tablet within one hour from exposure of the tablet to an aqueous medium.

7. The unit dosage form of claim 6, wherein the tablet is coated with a water resistant coating.

8. The unit dosage form of claim 6, wherein the surfactant is an ionic surfactant.

9. The unit dosage form of claim 6, further comprising a minor but effective amount of at least one of a second binder, a disintegrant, a glidant and a lubricant.

10. The unit dosage form of claim 9, further comprising about 0.5-5 wt-% polyvinylpyrrolidone.

11. The unit dosage form of claim 9, further comprising about 2.5-7.5 wt-% pregelatinized starch.

12. The unit dosage form of claim 9, further comprising about 0.1-0.75 wt-% silicon dioxide.

13. The unit dosage form of claim 9, further comprising magnesium stearate.

14. A therapeutic method for treating a human afflicted with narcolepsy, restless leg syndrome, essential tremor, fibromyalgia, or chronic fatigue syndrome by orally administering to said human an effective amount of a unit dosage form of claim 6.

15. A method for preparing the tablet of claim 1 by granulating a water-free composition comprising the sodium oxybate, the compression and the binder; and compressing the granulated composition to yield said tablet.

16. The method of claim 15 further comprising coating said tablet with a water resistant coating.

17. The method of claim 16 wherein the coating comprises PVA and lecithin.

18. A compressed tablet of an oxybate salt for oral delivery of 0.5-1.25 g of oxybate salt comprising 80-95 wt % oxybate salt; 5-10 wt % compression aid; and 1-50% binder; wherein the tablet is bioequivalent to sodium oxybate oral solution.

19. The tablet of claim 18 wherein the oxybate salt is selected from the group consisting of potassium oxybate, calcium oxybate, lithium oxybate and magnesium oxybate.

* * * * *